United States Patent [19]
Franzen et al.

[11] Patent Number: 5,608,217
[45] Date of Patent: *Mar. 4, 1997

[54] ELECTROSPRAYING METHOD FOR MASS SPECTROMETRIC ANALYSIS

[75] Inventors: Jochen Franzen, Bremen; Matthias Mann, Leimen; Matthias Wilm, Heidelberg, all of Germany

[73] Assignee: Bruker-Franzen Analytik GmbH, Bremen, Germany

[*] Notice: The term of this patent shall not extend beyond the expiration date of Pat. No. 5,504,329.

[21] Appl. No.: 402,125

[22] Filed: Mar. 10, 1995

Related U.S. Application Data

[63] Continuation-in-part of Ser. No. 401,405, Mar. 9, 1995, Pat. No. 5,504,329.

[30] Foreign Application Priority Data

Mar. 10, 1994 [DE] Germany ........................ 44 08 032.8
Nov. 25, 1994 [DE] Germany ........................ 44 44 229.7

[51] Int. Cl.⁶ ................................................ H01J 49/10
[52] U.S. Cl. .................................... 250/288; 250/281
[58] Field of Search ........................... 250/288, 288 A, 250/281, 423 R

[56] References Cited

U.S. PATENT DOCUMENTS

| | | | |
|---|---|---|---|
| 4,531,056 | 7/1985 | Labowsky et al. | 250/288 |
| 4,861,988 | 8/1989 | Henion et al. | 290/288 |
| 4,885,076 | 12/1989 | Smith et al. | 204/299 R |
| 5,115,131 | 5/1992 | Jorgenson et al. | 250/288 |
| 5,306,910 | 4/1994 | Jarrell et al. | 250/286 |
| 5,504,329 | 4/1996 | Mann et al. | 250/288 |

*Primary Examiner*—Jack I. Berman

[57] ABSTRACT

A method is provided for analyzing analyte ions in a liquid using a spectrometer incorporating an ion trap, using a capillary nozzle adjacent an inlet aperture for the ion trap. The liquid is electrosprayed from the capillary nozzle by generating an electric field at the nozzle to ionise the said analyte and produce a beam of charged spray particles, and the beam of charged particles is injected into the ion trap through the inlet aperture. The pressure within the capillary is such that flow of the liquid through the capillary occurs only in the presence of the said electric field, and flow of ions into the ion trap is controlled by varying the electric field.

19 Claims, 2 Drawing Sheets

ELECTROSPRAYING METHOD FOR MASS SPECTROMETRIC ANALYSIS

RELATED APPLICATIONS

This application is a continuation-in-part of U.S. patent application Ser. No. 401,405 entitled "Method of Ionizing Atoms or Molecules by Electrospraying," which has named inventors Matthias Mann and Matthias Wilm and was filed on Mar. 9, 1995 and which issued as U.S. Pat. No. 5,504,329. This application may be identified by Bookstein & Kudirka, P. C. Attorney Docket No. B0004/7014.

BACKGROUND OF THE INVENTION

FIELD OF THE INVENTION

This invention relates to the so-called "electro spray ionization" of molecules (frequently abbreviated to ES or ESI). This method is, in general, carried out by spraying aqueous solutions from a spray capillary under the influence of an electric field. The method is especially suited for the ionization of large molecules, especially bio molecules, and for their analysis by mass spectrometry after introduction into the vacuum system of the spectrometer.

DESCRIPTION OF THE RELATED ART

The conventional method of electrospray ionization, as recommended for commercially available instrumentation, operates in the following way:

A voltage of several kilovolts is applied between a metal capillary and a flush surface separated by a distance of approximately 20 to 50 millimeters. Under the effect of the electric field, a liquid in the capillary is dielectrically polarized at the end of the capillary and pulled out into a cone, the so-called Taylor cone. At the pointed end of the cone the surface tension of the liquid is no longer able to withstand the attraction of the electrical field, causing a small droplet, which is electrically charged due to dielectric polarization, to be detached. Under the effect of the inhomogeneous electrical field, the charged droplet flies greatly accelerated towards the flush counterelectrode, but is soon slowed down in the surrounding air. During the flight considerable evaporation occurs from the surface of the droplet. Should the liquid contain a few larger molecules, which can be charged (ionized) more easily than the molecules of the liquid, the larger molecules remain in ionized form after complete evaporation of the liquid. Under the effect of the electrical field, the ionized molecules fly on towards the counterelectrode due to the known process of "ion mobility" and can be transferred to the vacuum system of a mass spectrometer through a fine aperture or through a capillary.

Depending on the supply of liquid in the capillary, the droplets detach with great frequency, generally resulting in a continuous stream of charged particles or ions. The supply of liquid is maintained by a very uniformly operating pump, usually a syringe pump. Other systems use the electroosmotic pumping effect of capillary electrophoresis.

In this process, larger molecules are usually charged not only singly, but a number of times. As a rough rule, the average charge number increases in accordance with the size of the molecule. For the most part the charge is not ionization by electron abstraction, but by protonation, i.e. combination with charged hydrogen atoms $H^+$. For this reason, ionization also depends greatly on the hydrogen-ion concentration, i.e. on the pH value of the solution. There is usually a wide distribution around the average charge number with different numbers of charges.

The multiple charge of the large molecules and the wide charge distribution are particularly favourable for detection. Since most mass spectrometers have a limited mass range (or more precisely a limited range of mass-to-charge ratios), it is still possible, despite this limitation, to detect very large molecules well beyond the mass range defined for singly charged ions since the electro spray ions are charged a number of times. Due to the wide and regular distribution of the number of charges over molecular ions of the same isotopic mass pattern, it is easily possible to determine the molecular mass.

U.S. Pat. No. 5,115,131 and U.S. Pat. No. 4,531,056 describe ESI using a capillary, and are believed to represent the state of the art. These references and the other patents and literature articles cited in them are incorporated herein by reference. The closest state of the art concerned with electrospraying at ambient pressure is described in U.S. Pat. No. 4,531,056. U.S. Pat. No. 5,115,131 is concerned with electrospraying in vacuum. Under such conditions a kind of explosive evaporation of the solution takes place at the tip of the capillary under influence of the surrounding vacuum.

All presently known techniques of electrospraying teach that it is necessary (a) to take active steps to cause the solution to flow through the capillary and (b) to spray the outflowing solution (the "eluent") by a high electric voltage. This is emphasised in the claims of the patents referred to above. For example, the claims of U.S. Pat. No. 4,531,056 refer to causing the solution to flow through the capillary as an independent step.

U.S. Pat. No. 5,115,131 especially teaches that it is possible to operate, using external pumping of the solution, with extremely low flow rates in the range of 0.1 to 100 nanoliters per second (or 1 to 10 nanoliters per second in a narrower rage) by using capillaries with very fine tips. The patent does not teach how the ions can be introduced into the vacuum system of the mass spectrometer. Furthermore, the patent description is directed entirely to spraying in vacuum with its evaporation by the surrounding vacuum. There is no suggestion that it is possible to employ such low flow rates in ambient gas. Again, to "cause the solution to flow through the capillary" is an independent step in claim 1.

The flow in all these cases is generated by the operation of external pumps, most often a syringe pump, or a HPLC pump in case of coupling with HPLC. U.S. Pat. No. 4,885,076 describes the production of a flow by electroosmotic pumping in an electrophoresis capillary.

There are significant disadvantages in the existing prior art. Frequently in biochemistry and medicine only very small substance quantities are available for analyses (sometimes quantities of only a few femtomoles). Assuming however, a lower concentration limit of approximately 0.1 picomol per microliter and a minimum flow rate of one microliter per minute, the lower limit for the consumption of analyte is, however, approximately 100 femtomol per minute. Scanning, especially with the MS/MS method, usually takes several minutes. Several hundred femtomol of substance are therefore required. In routine methods these values rise by factors of 10 to 100, meaning that quantities of well over one picomol are regularly required.

Attempts to reduce the flow rate for electrospraying in ambient air at standard pressure, which with conventional and present commercially available instruments is at least approximately 1 microliter per minute, have failed so far since they did not achieve stable electrospray conditions. With the conventional method the flow rate is always determined by a pump. It is very difficult or impossible to stabilise the pumping process through the network of lines and connections at such extremely low flow rates.

Another disadvantage is the production of rather large droplets which need a long flight path for evaporation. The droplets have diameters of about 1 micrometer.

One improvement of this method which has been suggested involves surrounding the solution with a second liquid having a different surface tension using the aid of a coaxial capillary in order to thus achieve smaller droplets (U.S. Pat. No. 5,122,670). The coaxial feeding of a special additive spray gas to pneumatically assist spraying has also been proposed (U.S. Pat. No. 4,861,988, U.S. Pat. No. 5,170,053).

A further improvement which has been proposed is to assist the spraying process using ultrasound. This also results in somewhat smaller droplets.

It is, however, known to all specialists in the field that analyte is positively wasted in the conventional method of electro spraying. The long distance required for evaporation of the droplets necessarily results in considerable widening of the ion beam due to space charge repulsion so that only a small proportion of the ions (approximately $1/100$ to $1/1,000$) can be admitted through the fine aperture of the mass spectrometer.

Present electrospraying can be influenced by very many parameters of the solution used, most parameters having very narrow tolerance limits, outside of which stable operation is not possible. For example, highly pure water cannot be sprayed since its electrical resistance is too great. On the other hand, the addition of salts to increase conductivity is exceptionally critical. Normally, salt concentrations of less than one millimole per liter are employed. Salt solutions of over 10 millimole per liter cannot be used.

Aqueous solutions with high proportions of organic solvents, such as result from separation processes with liquid chromatography or gel chromatography, can also not be sprayed with the conventional method.

The range of pH values of the solution is also greatly limited, primarily to the slightly acid range. Owing to this limitation in pH, negative spraying, as is required for nucleotides, is not possible at all.

Some types of mass spectrometers, especially ion traps, do not need ion currents which are sustained for long periods of time. Ion traps are loaded in filling periods, and they are used then for investigations of the ions in the trap by various procedures. During these investigation periods, the delivery of ions from the spray process can be stopped. The conventional method of electrospraying, however, delivers a continuous flow of ions. There is no method known to switch the ion current on and off in a time scale of milliseconds.

SUMMARY OF THE INVENTION

In accordance with the invention, there is provided a method of analyzing an analyte present in a liquid using a mass spectrometer incorporating an ion trap, which method comprises providing a capillary with an outlet adjacent an inlet aperture for the mass spectrometer, electrospraying the liquid from the capillary outlet by generating an electric field at the outlet to produce a beam of charged spray particles, and injecting the beam of charged particles into the mass spectrometer through the inlet aperture. The pressure within the capillary is such that flow of the liquid through the capillary outlet occurs only in the presence of the said electric field, and wherein flow of charged particles into the mass spectrometer is controlled by varying the said electric field.

According to the invention, both the flow of substance solution through the spray capillary and the spray process itself may be switched on and off just by variations of the voltage for the electric field. For mass spectrometers which operate with cyclic phases of ion generation and ion analysis, as for instance all types of ion trap mass spectrometers, analyte consumption can be minimized by switching the spray process on during the trap filling phase, and by switching it off during the ion analysis phase. ICR mass spectrometers as well as rf quadrupole ion traps can be filled with ions in a way which consumes very low levels of analyte. Depending on the time ratio of both phases, substance consumption can be decreased by about one to two orders of magnitude.

The term "mass spectrometer incorporating an ion trap" as used herein is intended to mean not only mass spectrometers which rely on the ion trap in their detection method (referred to herein as "ion trap mass spectrometers") but is intended to include also other forms of mass spectrometers, such as time-of-flight instruments, which include an ion trap simply as a storage device.

Particularly useful results can be obtained by "tandem mass spectrometry" techniques (commonly abbreviated as "MS/MS"), in which ions of a preselected mass-to-charge ratio are filtered and fed to a fragmentation cell. In the fragmentation cell, these preselected "parent" ions are dissociated into neutral fragments and "daughter ions". The daughter ions are measured in a second mass spectrometric method. MS/MS techniques can be carried out as "tandem in time", in which, in a first time period, ions of a preselected mass-to-charge ratio will be "isolated" by the ejection of all other ions. The isolated ions can then be fragmented in a second time period, for example by exciting their secular oscillations in the presence of a collision gas. The daughter ions can then be measured in a third time period, resulting in a daughter ions spectrum of the parent ions.

The method may be carried out with the nozzle tip in ambient gas, and at standard pressure. In the method of the invention, flow of liquid is caused by the high electric field at the tip of the capillary nozzle. We have found that this flow is self-regulating and extremely stable, even at extremely low flow rates.

To achieve the desired flow without any external pumping, it is necessary to use a capillary with an extremely fine tip. Because of the self-regulation, extremely low flow rates of the solution in the order of 10 to 100 nanoliters per minutes can be achieved, with stable operation in wide ranges of solution parameters like viscosity, pH, salt concentrations or additions of organic solvents. Because of the fine tip, a very low distant to the counterelectrode can be maintained, and the slightly divergent beam of droplets can be introduced completely into the entrance opening of the mass spectrometer. Sample consumption for measurements is lowered by about two orders of magnitude, compared with recommended methods on commercially available instruments.

In accordance with the invention, a glass capillary may be employed for the electrospray method as in U.S. Pat. No. 5,115,131, which is pulled out into a very fine tip with an aperture diameter of only approximately 2.5 micrometers in an automatic pulling apparatus of the kind used to manufacture very fine capillary tips for cell microinjections. The outside diameter of the tip may be approximately 4 micrometers. The tips and shaft of the capillaries may be coated with a thin conductive layer, for example, a gold layer to enable them to conduct well on the outside. Such coatings may for example, be applied by sputtering in a vacuum.

Experiments with such very sharply pointed capillaries have produced results which do not conform with the expectations from state-of-the-art knowledge.

With low-viscosity liquids (for example, water/methyl alcohol mixture) flow of solution may be produced by electrical pulling forces alone, resulting in self-regulation of the flow providing a very constant ion current. With higher viscosity liquids a slight overpressure of gas at the end of the capillary is sufficient to achieve a self-regulating flow. The slight gas overpressure alone is insufficient to maintain the flow without the presence of the spray voltage.

In contrast to the teaching of above-mentioned patents, it is not necessary to cause the solution to flow through the capillary independent of the spray process caused by the high electric voltage. In contrast, for the achievement of extremely low flow rates any external pumping proves to be counter-productive because the spray process immediately became unstable.

Under these conditions, the electric field is able to produce, in a very stable process, droplets of about 200 nanometers or smaller in diameter at the tip of the glass capillaries. Such droplet diameter is smaller by a factor 5 to 10, and the volume and mass smaller by a factor 125 to 1000 as compared with conventional methods.

With this new method of electrospraying without forced generation of solution flow through the capillary by an external pump, the ion beam can be easily switched on and off. We have found that, typically, the ion beam can be switched off completely by lowering the voltage difference by approximately 200 volts and can be restored again to its previous level by increasing the potential difference to the original value. Switching on and off can each be performed in less than one millisecond.

This switching technique enables storage mass spectrometers such as ion cyclotron resonance spectrometers (ICR) or rf quadrupole ion traps to achieve further improved utilization of low substance quantities.

The optimal distance between the tip and counterelectrode is approximately 1.5 millimeters. Under such conditions, the droplets evaporate over a distance of only approximately one millimeter with beam broadening of only approximately 200 micrometers, enabling them to be transferred almost entirely through a conventional capillary with 500 micrometer inner diameter into the vacuum of the mass spectrometer.

Due to the low distance from the capillary nozzle to the counter-electrode, the electric field required can be produced with a spray voltage of below 1,000 volts, typically only approximately 600 to 800 volts, resulting in a much simpler power supply, relatively easy switching and control, facilitating fast switching.

The gas flow in a capillary inlet of a mass spectrometer for conventional electro spray ionization is approximately one liter of ambient gas per minute. Nitrogen is mostly used, enabling approximately one gram of gas to be introduced per minute. The solvent flow of 25 nanoliters corresponds, however, to a mass flow of only 25 micrograms per minute. Even if the entire solvent were to be introduced into the mass spectrometer, it would only correspond to a weight concentration of 0.0025%.

Thus, by the use of the method of the invention, the need for a special counterflow of pure gas to keep large quantities of solvent away from the mass spectrometer is eliminated. The counterflow is required only if last traces of the solvent have to be eliminated, or if the last remains of solvate molecules have to be removed. This is not required with all mass spectrometers. For example, in ion trap mass spectrometers, solvating molecules can be removed in the trap itself. The solvating molecules have also been successfully removed in heated inlet capillaries of the mass spectrometer.

By filling the capillary with 1/10 microliter (about 3 mm liquid in a capillary with 200 micrometer inner diameter) and with a concentration of 0.05 picomol of protein per microliter, i.e. with a substance quantity of only 5 femtomoles of protein, it is possible to work uninterruptedly for approximately six minutes. If the spraying process restricted to ion filling periods of ion trap mass spectrometers only, the working period is prolonged to one full hour, if the ratio of filling and analysis is about 1:10. In this time even complex amino acid sequence analyses can be performed. Both types of ion trap mass spectrometers are especially suited for this kind of work requiring MS/MS techniques.

Solutions with concentrations of approximately 0.1 to 0.5 picomol per microliter can be sprayed routinely, i.e. without special measures for optimal adjustment of all parameters.

BRIEF DESCRIPTION OF THE DRAWINGS

A number of preferred embodiments of the invention are illustrated in the accompanying drawings, in which.

DETAILED DESCRIPTION OF A PREFERRED EMBODIMENT

Figure 1:
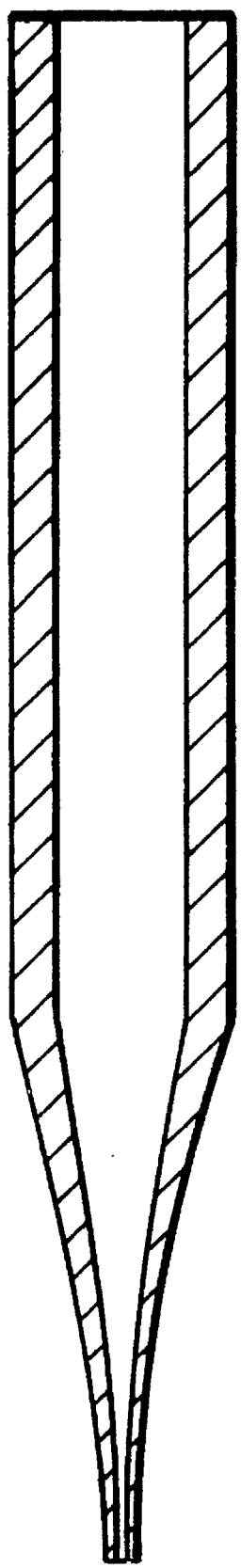
FIG. 1 is a schematic representation of a capillary nozzle for use in this method.

Referring first to FIG. 1, a normal glass capillary was pulled out to a tip in an automatic unit of conventional kind. This pulling-out process is very reproducible. The tip of the capillaries was then coated with gold in a vacuum by sputtering. The gold layer extends right into the cylindrical section in order to create a voltage contact. FIG. 1 is intended only to illustrate the principle, and the various parts are not necessarily in proportion.

Figure 2:
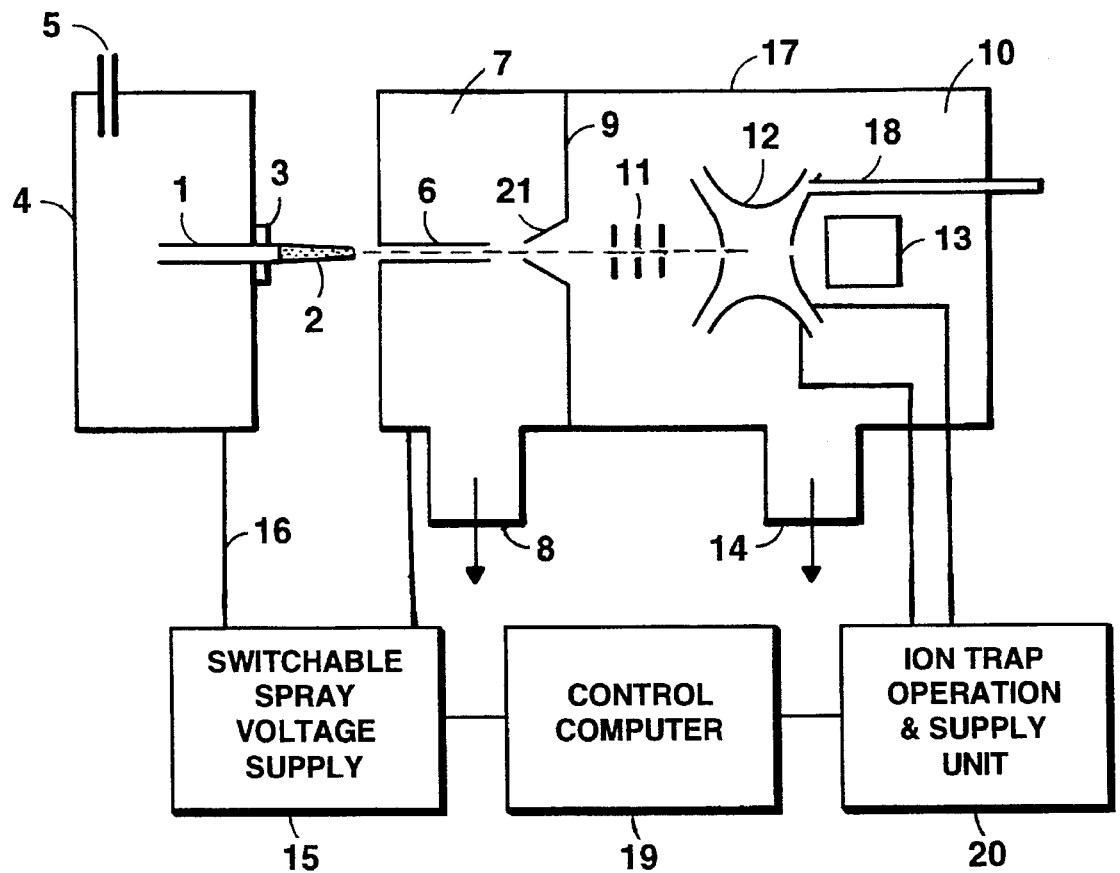
FIG. 2 is a schematic drawing of a mass spectrometer for carrying out the method of the invention.

Referring to FIG. 2, a spray capillary 1 is provided, having a fine tip 2, with a nozzle outlet, having an inner diameter of 2.5 micrometer. The spray capillary 1 is mounted in a sealed chamber 4, by means of a seal 3. Gas chamber 4 may be pressurised by means of a gas line 5. A switchable voltage supply 15 provides a variable voltage between nozzle 2 and an inlet capillary 6 of a mass spectrometer, shown generally at 17. Main chamber 10 of spectrometer 17 is evacuated by vacuum pump 14. Capillary 6 opens into a differential pumping chamber 7, connected to a vacuum pump indicated schematically at 8. A dividing wall 9 separates differential pumping chamber 7 from the main mass spectrometer chamber 10, and holds back most of the gas streaming into the mass spectrometer through the capillary, as well as the charged particles. The distance between the tip of spray nozzle 2 and the inlet of capillary 6 is approximately 1.5 mm.

Charged particles enter the main mass spectrometer chamber 10 through skimmer aperture 21. A lens system 11 focuses the charged particle beam into an ion trap 12, where the particles are arrested by a damping gas, fed via gas line 18.

In use, capillary 1 is partially filled with a small amount of liquid containing a solution of the analyte. Capillary 1 is then sealed in chamber 4 by means of seal 3. A voltage is then applied between spray nozzle 2 and capillary 6, so as to cause ions of the analyte to enter ion trap 12. When a sufficient number of ions have entered the ion trap 12, the spray voltage is decreased, under the control of control computer 19, until the flow of liquid through nozzle 2 ceases. The pressure applied to gas line 5 is insufficient to generate flow of liquid through capillary nozzle 2, in the absence of the spray voltage.

The mass spectrum of particles inside the ion trap is then investigated, by a conventional ion trap technique, under the control of ion trap operation and supply unit 20, and a mass spectrum is obtained, using ion detector 13. After a mass spectrum has been obtained, a new filling cycle is commenced, under the control of control computer 19, by increasing the spray voltage such as to refill the ion trap.

Typically, the beam of charged spray particles can be switched on or off within a single millisecond, by lowering the spray voltage by about 200 volts. When the voltage is restored to its original value, the spray particle current returns within a millisecond to within a few percent of its original value.

One preferred method comprises the following steps:

Spray capillaries with an outside diameter of 300 micrometers, inside diameter of 200 micrometers, and length of 50 millimeters were used. After being cleaned carefully, appropriate capillary glass was pulled out to a fine tip with an outside diameter of 4 micrometers and a fine aperture of 2.5 micrometers on an apparatus for the manufacture of microinjection pipettes. The spray capillaries are then coated in a vacuum with a very thin gold layer less than 1/10 micrometer thick which is applied by sputtering.

The spray capillaries can be used without any further cleaning. The process of pulling them out into a tip is already a very good cleaning procedure. The inner surface can, however, also be silanized with conventional methods to prevent adsorption of the molecules for investigation. Any other method of making the surface adsorption inert can be used too.

The spray capillaries were filled with a micropipette having an outside diameter of approximately 150 micrometers. The solution was forced right into the inner cone which is formed by the pulled-out tip. With very small amounts of substance in solution, small droplets of the solution (about 1/10 microliter) can be simply drawn into the capillary by capillary forces.

The rear of the filled spray capillary was then immediately fastened in a seal bushing of a small housing and sealed in the usual manner by tightening a sealing screw. At the bottom of this housing was a small amount of solvent, saturating the gas in the housing with solvent. Saturation with solvent is to prevent the spray capillary from drying out from the rear, even when in operation for extended periods and also during intermissions. The housing was then pressurized via a gas inlet, forcing the solution in the spray capillary right to the very front of the tip. The gas pressure can then be relieved a little without causing the solution to run back from the tip. The remaining gas pressure has to be fine-tuned to such a value not causing any flow of solution out of the capillary tip. The front face of the capillary tip should be covered with a hydrophobic layer hindering the solution to flow out of the tip by capillary forces.

There is no danger of the spray capillary drying out at the front since the liquid surface is more than 4 powers of ten smaller here.

The seal of the spray capillary in the housing was designed so as to create an electrical contact with the metal layer of the tip. A voltage was thus applied to the tip. This voltage creates the electric field.

Air can be used as the pressurizing gas. An inert gas, for example, nitrogen, is recommended for substances sensitive to oxidation.

The spray capillary was fastened in the housing in such a way that its tip precisely projects from the housing by a preselected distance which is toleranced to approximately 0.1 millimeter.

The housing was then brought near to the flush counterelectrode on a precision guide. A limit stop arrests the housing when the tip is precisely 1.5 millimeters away from the counterelectrode. Due to the precision guide, the tip is automatically centred with respect to the aperture in the counterelectrode. The tolerance for centering is approximately 1/20 millimeter, centering not therefore being extremely critical.

Optimal admission into the mass spectrometer was provided by an inlet capillary approximately 20 centimeter long made of insulating material with a capillary aperture of approximately 500 micrometers and coated at both ends with a metal layer covering the end face and part of the cylindrical section. These inlet capillaries are already used in conventional electrospray ionization.

Switching on the voltage between the tip of the spray capillary and the counterelectrode starts the droplet jet and ion beam. The spray voltage is approximately 600 to 800 volts. Although the voltage is only slightly dependent on the distance from the tip to the counterelectrode, it is very dependent on the type of solvent. The mass spectrometer device for measuring the total ion current can be used to set the correct voltage. No other adjustment of the method is necessary.

In this type of analysis of protein molecules, concentrations of approximately 0.1 to 0.5 picomol per microliter can routinely be used. The consumption of solution is approximately 25 nanoliters per minute, and this can be readily controlled by the spray voltage. With half a microliter of solution, i.e. with substance quantities of 50 to 250 femtomol, it is possible to work uninterrupted for approximately half an hour. The consumption of substance is thus approximately 10 to 100 times lower than in conventional electrospray methods.

Ion-storage mass spectrometers, such as ICR spectrometers or rf quadrupole ion traps, operate with cyclic charging phases which are then interrupted by phases in which the actual ion investigation and scan is carried out. The charging phases last for 5 to 20 milliseconds on average, investigation and scan phases for approximately 200 milliseconds up to 1 second (and even more). Since the ion current needs to be switched on only in the charging phase, the consumption of substance is reduced by a factor of about 1 to 2 orders of magnitude. Such switching cannot be carried out in the conventional method of electro spraying.

As stated above, with about 3 mm solution in a capillary with 200 micrometer inner diameter, and with a concentration of 0.05 picomol of protein per microliter, it is possible to work uninterruptedly for approximately six minutes. This is a substance quantity of only 5 femtomoles of protein. With the spraying process is restricted to ion trap filling periods only, the working period is prolonged to one full hour, if the ratio of filling and analysis is only about 1:10. In this time even complex amino acid sequence analyses can be performed with both types of mass spectrometers.

Cleaning of the spray capillaries used is critical since, despite careful cleaning of the small tubes, it is very easy for wall-adsorbed molecules of former samples with different pH values of the solution to be measured since the concentrations used are extremely low. It is therefore advisable to use the spray capillaries once only.

Further improvements of the method concern the automation of sample feeding, it being possible to feed the sample both from a separating chromatograph (liquid chromatography, gel chromatography, electrophoresis) and by the supply of filled spray capillaries.

The spraying method is very stable and only slightly dependent on salt concentrations. Thus, salt concentrations of 100 millimole per liter were easily sprayed. Although the salts, of course, occur as ions in the spectrum, the spectra can still be interpreted well.

The spraying process is also barely influenced by pH values. Solutions ranging from pH 1 to pH 12.5 have been successfully processed, making negative spraying also possible for the production of negatively charged ions, including, for example, ions of the kind favourable for nucleotides.

Even aqueous solutions with larger proportions of organic solvents, such as 30% acetonitrile or methanol, were sprayed with this method.

The operation at ambient air and standard pressure allows for easy changes of the capillaries, in contrast to the operation in vacuum. In trace analysis work, the use of clean capillaries is important, and cleaning of the capillaries is by no means easy. Thus the use of one-way capillaries is advantageous.

The capillaries can be easily and reproducibly pulled out into tips if automatic units of the kind developed to manufacture very fine capillary tips for microinjections are used. The ease of manufacture suggests using these capillaries once only, especially since the analysis of solutions with extremely low concentrations would require extremely stringent cleaning methods. Industrial manufacture of the capillaries would be worthwhile.

Due to the small distances between the capillary tip and the fine aperture to the mass spectrometer, the capillary can be adjusted very easily. It has proven sufficient to make only a mechanical adjustment without simultaneously observing the ion current, making the method especially suitable for feeding samples automatically.

In accordance with at least the preferred embodiment of the invention, it is possible to achieve solvent flows and thus the consumption of analyte, was 40 times lower than the minimum flow which can be stabilized with conventional methods. Stable operation was possible with a flow rate of 25 nanoliters per minute only.

Compared with a conventional electro spray apparatus which operated with a solution of the same concentration, the ion current in the mass spectrometer was approximately two to three times higher.

At a flow rate of only 25 nanoliters per minute it was possible to obtain good protein spectra with the exceptionally low concentration of only 0.05 picomol per microliter. This corresponds to a substance flow rate of only 1.3 femtomol per minute, more than 70 times lower than the lowest values for the conventional technique.

From droplet diameter, flow rate and concentration it can be calculated that there is only approximately one protein molecule per droplet, which then takes over the entire charge of the droplet. The spectra barely differed from those obtained using the conventional electrospray technique.

From the above values it can be estimated that a flow of 25 nanoliters per minute generates, from a solution with 0.05 picomole per microliter and with about 10 elementary charges per molecule, an ion current of about $10^8$ elementary charges per second. A rf quadrupole ion trap takes up about $10^5$ elementary charges before space charge effects show a bad influence on spectrum measurements.

While the invention has been shown and described with regard to a preferred embodiment thereof, it will be understood by those skilled in the art that various changes in form and detail may be made therein without departing from the spirit and scope of the invention as defined by the appended claims.

What is claimed is:

1. A method of analyzing an analyte present in a liquid using a mass spectrometer incorporating an ion trap, the method comprising:

providing a capillary with an outlet adjacent an inlet aperture for the mass spectrometer;

electrospraying the liquid from the capillary outlet by generating an electric field at the outlet to produce a beam of charged spray particles; and injecting the beam of charged particles into the mass spectrometer through the inlet aperture, wherein the pressure within the capillary is such that flow of the liquid through the capillary outlet occurs only in the presence of said electric field, and wherein flow of charged particles into the mass spectrometer is controlled by varying the said electric field.

2. A method as claimed in claim 1, wherein the flow of charged particles into the ion trap is controlled cyclically so as to switch on the flow of charged particles in filling periods of the ion trap, and to switch off the flow during time periods for ion investigation and analysis.

3. A method as claimed in claim 1, wherein spraying is carried out with the capillary outlet in ambient gas at standard pressure.

4. A method as claimed in claim 1, wherein the capillary forms a nozzle with an outlet diameter smaller than 5 micrometers.

5. A method as claimed in claim 4, wherein the nozzle outlet diameter is from 2 to 4 micrometers.

6. A method as claimed claim 1, wherein the spectrometer is an ion trap mass spectrometer.

7. A method as claimed in claim 6, wherein the ion trap mass spectrometer is an ion cyclotron resonance mass spectrometer, or an rf quadrupole mass spectrometer.

8. A method as claimed in claim 1, wherein substantially the whole of the beam of spray particles is transferred to the mass spectrometer through the aperture.

9. A method as claimed in claim 1, wherein the flow rate of the liquid is lower than 1000 nanoliters per minute.

10. A method as claimed in claim 9, wherein the flow rate of the liquid is lower than 25 nanoliters per minute.

11. A method as claimed in claim 1, wherein the capillary is pressurised to a static pressure which is insufficient to maintain flow through the capillary in the absence of the said electric field.

12. A method as claimed in claim 11, wherein the static pressure is maintained by a closed gas volume at the end of the capillary.

13. A method as claimed in claim 1, wherein the potential difference used to generate the said electron field is less than 1 kilovolt.

14. A method as claimed in claim 1, wherein the capillary outlet and the aperture are less than 3 millimeters apart.

15. A method as claimed in claim 1, wherein the aperture of the mass spectrometer is 500 micrometers or less in diameter.

16. A method as claimed in claim 1, wherein an additional gas is supplied to the space between capillary outlet and the aperture.

17. A method as claimed in claim 16, wherein the additional gas flows in a direction counter to the beam of spray particles.

18. A method as claimed in claim 16, wherein the additional gas is supplied at super-ambient temperature.

19. A method as claimed in claim 16, wherein the pressure in the capillary is ambient pressure.

* * * * *